(12) United States Patent
Zelechonok et al.

(10) Patent No.: US 7,125,489 B2
(45) Date of Patent: Oct. 24, 2006

(54) HPLC COLUMN DESIGN AND METHOD OF MAKING SAME

(75) Inventors: Yury Zelechonok, Northbrook, IL (US); Mikhail Alkhovsky, Niles, IL (US); Vladislav Orlovsky, Wheeling, IL (US)

(73) Assignee: SIELC Technologies Corporation, Prospect Heights, IL (US)

( * ) Notice: Subject to any disclaimer, the term of this patent is extended or adjusted under 35 U.S.C. 154(b) by 160 days.

(21) Appl. No.: 10/797,587

(22) Filed: Mar. 11, 2004

(65) Prior Publication Data

US 2005/0199540 A1    Sep. 15, 2005

(51) Int. Cl.
*B01D 15/08*    (2006.01)
(52) U.S. Cl. .................................... 210/198.2; 210/656
(58) Field of Classification Search ............. 210/198.2, 210/656, 635, 232, 238; 96/101, 104, 106
See application file for complete search history.

(56) References Cited

U.S. PATENT DOCUMENTS

| | | | | |
|---|---|---|---|---|
| 3,682,315 A * | 8/1972 | Haller | ......................... | 210/233 |
| 4,093,550 A * | 6/1978 | Stahl et al. | .............. | 210/198.2 |
| 4,187,177 A * | 2/1980 | Stahl | ....................... | 210/198.2 |
| 4,283,280 A * | 8/1981 | Brownlee | ................. | 210/198.2 |
| 4,313,828 A * | 2/1982 | Brownlee | ................. | 210/198.2 |
| 4,389,313 A * | 6/1983 | Charney et al. | ......... | 210/198.2 |
| 4,451,364 A * | 5/1984 | Higgins et al. | .......... | 210/198.2 |
| 4,563,275 A * | 1/1986 | McEachern | .............. | 210/198.2 |
| 4,758,340 A * | 7/1988 | Marchand et al. | ....... | 210/198.2 |
| 4,855,047 A * | 8/1989 | Firth | .......................... | 210/232 |
| 4,876,005 A * | 10/1989 | America | .................. | 210/198.2 |
| 4,968,421 A * | 11/1990 | Spacek et al. | ........... | 210/198.2 |
| 5,194,225 A * | 3/1993 | Muller et al. | ................. | 422/70 |
| 5,238,556 A * | 8/1993 | Shirkhan | ................. | 210/198.2 |
| 5,472,598 A * | 12/1995 | Schick | ..................... | 210/198.2 |
| 5,534,152 A * | 7/1996 | Schick | ........................ | 210/656 |
| 5,651,885 A * | 7/1997 | Schick | .................... | 210/198.2 |
| 5,714,074 A * | 2/1998 | Karlsson et al. | ............. | 210/656 |
| 5,736,036 A * | 4/1998 | Upchurch et al. | ....... | 210/198.2 |
| 6,171,486 B1 * | 1/2001 | Green et al. | ............. | 210/198.2 |
| 6,615,989 B1 * | 9/2003 | Brown et al. | ............... | 210/443 |
| 6,783,673 B1 * | 8/2004 | Horsman et al. | ........ | 210/198.2 |

* cited by examiner

*Primary Examiner*—Ernest G. Therkorn
(74) *Attorney, Agent, or Firm*—Charles F. Lind

(57) ABSTRACT

The disclosed HPLC column is formed with overlying concentric inner and outer tubes. The flow path is established via the inner tube bore that holds packed absorbent, end filters and capping sealing members, and end coupling members cooperate with the inner tube at its ends. The sealing and end coupling members have conventional configurations for establishing a sealed connection with capillary lines and their fittings, for the series flow testing use through the column. The inventive method and manner of assembly provides that the outer tube overlies all of the inner tube and both sealing members, but only part of each end coupling member. The ends of the outer tube are then deformed radially inward to become mechanically interlocked with the end coupling members, as the column, holding also the filters and sealing members within the inner tube.

4 Claims, 2 Drawing Sheets

HPLC COLUMN DESIGN AND METHOD OF MAKING SAME

FIELD OF THE INVENTION

This invention relates to the high performance liquid chromatography technology (herein referred to as HPLC), and more specifically to the separation column(s) used therein.

BACKGROUND OF THE INVENTION

HPLC technology is widely used to detect and identify different components contained in a test sample or specimen material. A typical HPLC instrument has a high pressure pump for forcing a suitable solvent, via capillary lines, at a constant flow rate serially through a sampler, a separation column and a UV or other type detector. Periodically, a small quantity of the test sample will be injected via the sampler into this flowing solvent stream to travel then somewhat as a slug with the solvent stream into the separation column. The separation column contains an absorbent reactive anticipated sub phase components in the test sample. Thus, the different sub phases pass through the detector at different rates, producing separated flow through the detector suited for identification and quantitative analysis.

Different separation columns are commercially available for different testing needs, being of different lengths and/or diameters, and/or being packed with different absorbents and/or to different degrees of compactness.

A typical separation column consists of a rigid tube having couplings secured relative to its opposite ends, where each coupling has an internally threaded end cavity and capillary line adapter. A tubular exteriorly threaded fitting, snugged over an end of a capillary line, can be tightening into the column end coupling for establishing a reliably liquid-tight connection therewith. This allows the column to be easily connected into the HPLC instrument in a series flow circuit with the capillary line between the sampler and detector.

The column tube bore has a substantially uniform diameter (such as between 0.5 mm to 7 mm) machined and polished to a high finish. The tube bore is densely packed with the absorbent of micron sized particles, and sintered or mesh filters made of steel, titanium or PEEK close or cap at both tube ends. A sealing member secured or pressed onto the tube end generally holds the filter in place across the bore end.

The column provides high resistance to the liquid test sample mixture flowing through it, requiring pumped liquid pressures up to 5,000 psi, although only a small quantity of liquid sample is used (a few mcls) for each test. To withstand blow-out forces due to these high operating bore pressures, each end coupling must be mechanically secured relative to the tube.

To achieve this solid mechanical connection, some end couplings are threaded onto the tube ends while others utilize a stop ring compressed on the tube exterior for holding one component of a conventional threaded two-component fitting connection. However, thread machining adds costs, as does machining needed to form the multi-faced fittings (hex shapes or the like) for defining faces to accept a wrench or other tool for tightening the threaded components together.

Several problems can occur with separation columns having the above noted end couplings. For example, the column must have an identification label secured to it to identify its parameters. Such labels commonly have been taped around and onto the mid-portion the bore tube between the end couplings. This limits the shortest length column to several centimeters, as the smallest label and each end coupling might extends about a centimeter along the tube length, and label cannot cover the end couplings.

Further, it is desirable during certain testing procedures to maintain the column at a specific temperature, and present procedures place the column then on a flat heating or cooling plate held at that desired temperature. However, as the end couplings project radially beyond the tube exterior, only they contact the thermal plate (while the column mid-section is gapped from the thermal plate), meaning temperature uniformity along the column length remains uncertain.

OBJECTS AND SUMMARY OF THE INVENTION

A basic object of this invention is to provide an improved HPLC column defined by a column tube and couplings held relative to the column tube ends, where the maximum exterior radial column surfaces will be the column tube, not the end couplings, and can be uniformly cylindrical substantially end to end for economical and easy fabrication and labeling even the short 10 mm columns.

Another object of this invention is to provide an improved HPLC column having structures connecting the column tube and end couplings together, such structures being economical to make as components and easy and reliable to install in forming the column, and providing a generally uniform cylindrical column exterior substantially end to end.

Basic features of this invention to accomplish these objects include forming an HPLC column having inner and outer concentric tubes, with the inner tube defining the column bore with absorbent packed therein and with filters and sealing members cooperating with and capping the inner tube ends with packed absorbent therein, and with the outer tube overlying the inner tube and part of each end coupling operable to cooperate therewith to mechanically hold the end couplings relative to both the inner and outer tubes, while the outer tube defines the exterior column surface substantially end to end.

A further important feature of this invention is to provide that the outer tube, when positioned over the inner tube, can be deformed at each end radially inwardly to mechanically interlock with the adjacent end couplings, for easily, economically and reliably securing the end couplings in forming the column.

Yet another feature of this invention is that the improved HPLC column and method of making it can be used to form different size columns, changing only the tube lengths and bore diameters, and absorbents, but still merely overlapping the inner tube with the outer tubes and deforming the outer tube over part of the end coupling to retain the end couplings relative to the inner tube.

BRIEF DESCRIPTION OF THE DRAWINGS

These and other objects, features or advantages of the invention will be more fully understood and appreciated after considering the following description of the invention, which includes the accompanying drawings, wherein.

DETAILED DESCRIPTION OF THE INVENTION

Figure 1:
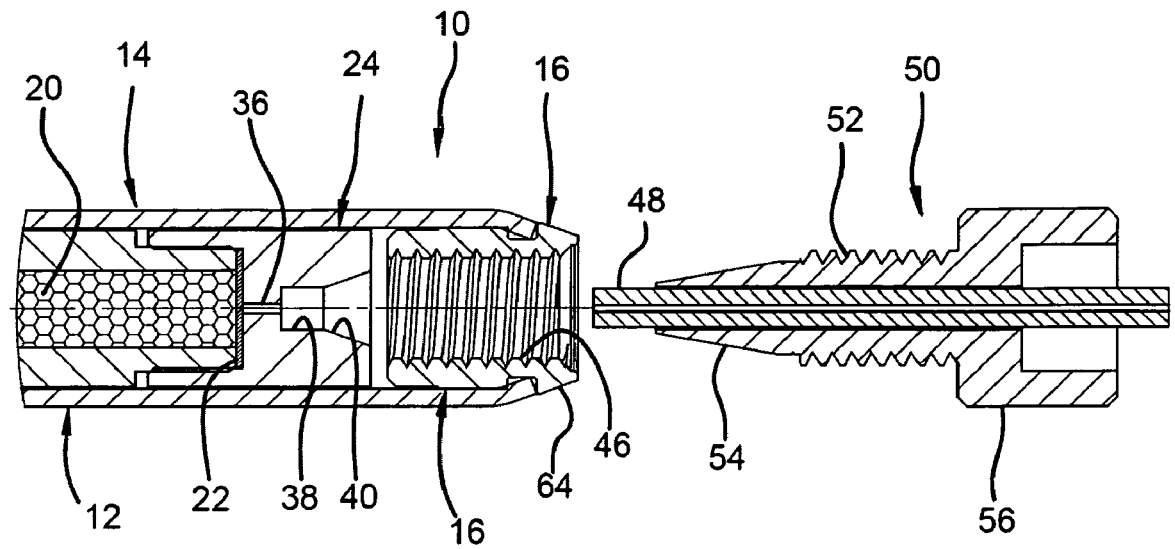
FIG. 1 is a sectional view of one end of the improved HPLC column (the other end being virtually identical), showing also in section a capillary line with its fitting snugged thereon in spaced pre-installed association with the column.
Figure 2:
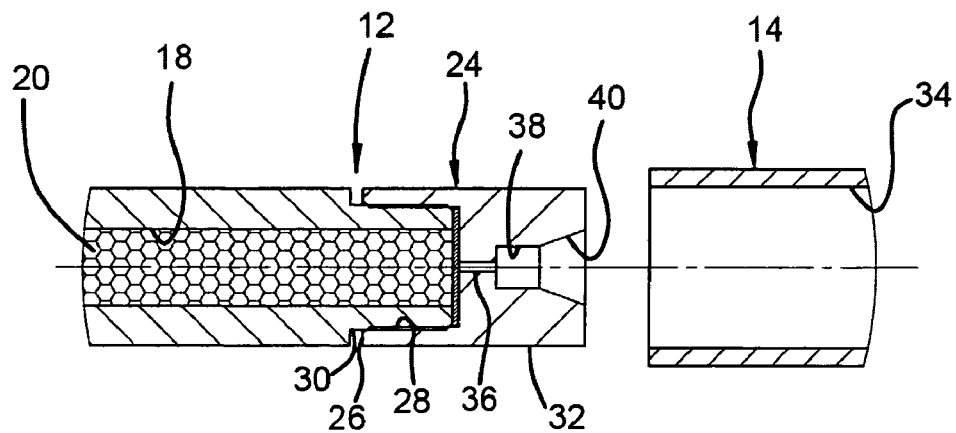
FIG. 2 is a sectional view of the inner tube, filled with absorbent and capped, and the outer tube, but in pre-installed association before being telescoped together in forming the improved HPLC column.

In describing this invention, the structural needs of the identified components to be noted herein are well known to those common to the industry. For example, the tubes and end couplings conventionally might be of stainless steel; the filter might be of mesh or a sintered material having micro-sized particles, such as stainless steel, titanium, or a durable plastic such as poly-ether-ether-keton (PEEK); and the resilient sealing structure might also be of a durable plastic or PEEK.

The improved HPLC column 10 is comprised of an inner tube 12 and an outer tube 14 telescoped together, and end couplings 16 sealed adjacent or secured relative to the ends of the tubes.

The inner tube 12 has a through bore 18 of uniform diameter from end to end with highly polished or finished inner surfaces. An absorbent 20 of micro-sized particles is densely packed in this bore 18. A mesh or sintered filter 22 is located crosswise to the bore 18, for substantially closing its open end and butting solidly against the packed absorbent 20. The filter 22 could also overlap and butt solidly against the end of the inner tube 12.

A resilient sealing member 24 (of durable plastic or PEEK) snuggly holds and supports the filter 22 in the above noted operative association with the inner tube, such as in an inwardly open end cavity or pocket. The sealing member 24 further serves the purposes of capping the filled but uninstalled inner tube 12, and later when the inner tube is assembled into the outer tube, of sealing the inner and outer tubes together so that the defined flow path through the column is leak-proof.

To reliably provide for this, sealing member 24 has an inwardly extended peripheral wall 26 with an inner cylindrical surface 28 suited to be telescoped tightly and sealingly onto a machined radially recessed outer cylindrical surface 30 of the inner tube 12. It also has an outer cylindrical surface 32 suited to telescope snuggly along the inner cylindrical surface 34 of outer tube 14. The sealing member 24 further has a cross wall with a fine opening 36 extended axially (and outwardly when assembled in the column) away from the filter 22 to exit into a larger axially extended cylindrical cavity 38 that then exits into a centered diverging conical cavity 40.

Each end coupling 16 has a cylindrical end section 44 sized to be press fit into the open end of the outer tube 14, for cooperating then with its inner surface 34. As so positioned, a centered threaded through bore 46 therein lines up with the conical cavity 40. These configurations, the threaded bore 46, cylindrical and conical cavities 38, 40, and opening 36 are comparable to conventional columns, in cooperating with and sealingly and mechanically securing a capillary line 48 and its surrounding end fitting 50 (both illustrated in FIG. 1), with external threads 52 and converging conical nose 54. The fitting 50 can be finger tightened into the column 10 via cylindrical knurled surface 56.

The end coupling 16 further has an intermediate annular groove 58 having an axial base surface and spaced radial surfaces. The distance between the radial surfaces (or groove width) should be wider than the thickness of the outer tube wall. Further, the corner edge 60 of the inward radial groove surface lines up generally with the cylindrical surface of end section 46 (and/or the outer tube inner surface 34), while the corner edge 62 of the endward radial groove surface might preferably extend radially beyond corner edge 60 by a distance typically less than the outer tube wall thickness. The outward end section of the end coupling 16 has a conical surface 64 converging from its largest diameter at the groove corner edge 62 to a radial end surface 66.

The outer tube 14 will have a length sized to overlie all of the inner tube 12 and both sealing members 24 and part of both end couplings 16, to have its ends line up above the grooves. Bottoming of the outer tube end against the outward groove surface with its corner edge 62 can be used to know exactly when this happens when pressing the end coupling into the outer tube. The end couplings need not bottom solidly against the sealing member, but the resilient sealing member will allow some axial leeway during the assembly step.

Figure 3:
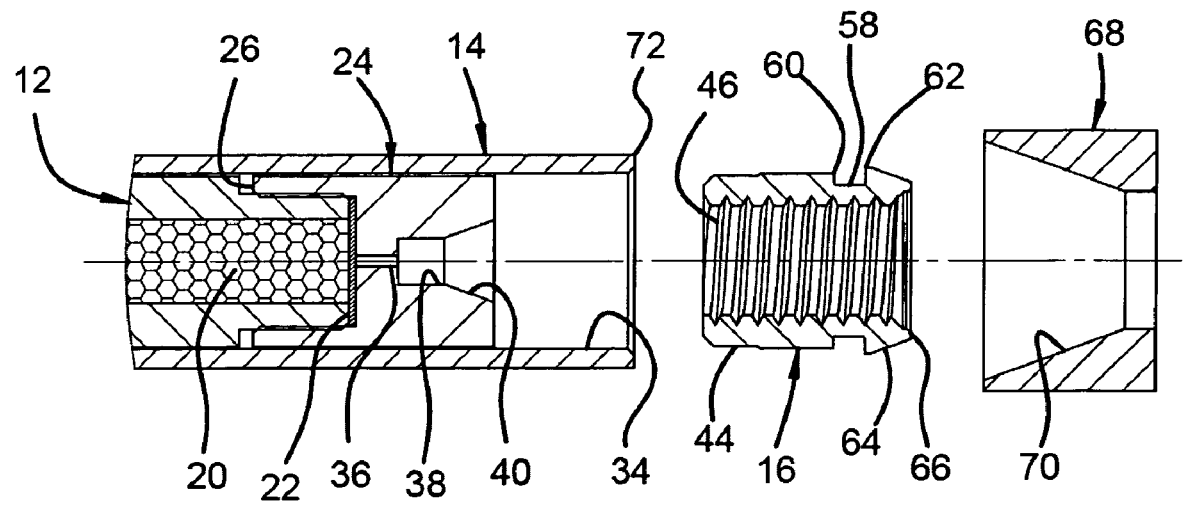
FIG. 3 is a sectional view of pre-installed components used to form the column; showing also a tool suited for deforming the outer tube onto the end coupling in forming the column.
Figure 4:
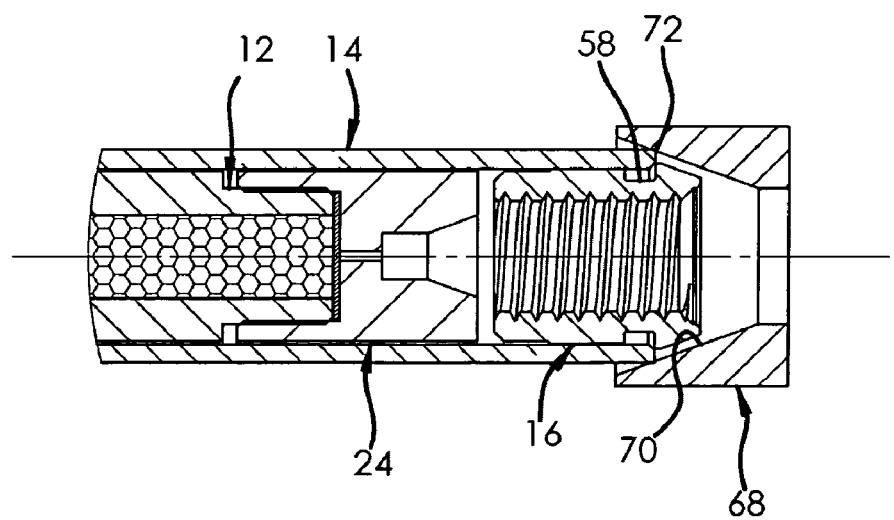
FIG. 4 is a sectional view of the inner and outer tubes in a position just prior to where the outer tube would be deformed onto the end coupling in forming the column.

A tool 68 is illustrated in FIGS. 3, 4 that might be used for biasing the end coupling into the outer tube but also then deforming the outer tube. The tool 68 has a conically diverging face 70 extended radially beyond the outer tube 14, being angled the same as (or slightly smaller than) the diverging angle of the end coupling end surface 66. The diverging face 76 of the tool will engage the protruding outer corner edges 72 of the outer tube 14 and deform the tube radially into the groove. However, the end coupling can be shifted axially within the outer tube, so that the outer tube might continue to be deformed radially around the inward groove corer edge 60 and into the groove, until the outer tube end bottoms against the radial and bottom groove surfaces, whereupon axial tool movement should be stopped.

The outer tube wall will be malleable to the extent to accept this slight deformation without failure. Moreover, the deformed outer tube will snuggly overlie the inward corner edge 60 of the groove operable to solidly anchor the outer tube relative to the end coupling. As so positioned and anchored, the end coupling will also be in sealed and axially constrained association with the inner tube, to provide a leak-proof column flow path.

The column might be made or assembled as follows. The inner tube 12 of the column 10 might be filled with absorbent and capped with the filters and sealing members, while yet being separate from the outer tube 14. This can be done by closing one bore end of the inner tube with its end filter and its sealing member held in place in an appropriate fixture (not shown), and by pumping under high pressure via a filling apparatus (not shown) a slurry mixture of the absorbent into the opposite open inner tube bore end. After the filled absorbent 20 becomes solidified as needed, the opposite open end of the bore 18 can be capped with its end filter and sealing filter holder. This filled and capped inner tube can them be pressed into a properly sized outer tube, sandwiched between the end couplings, and the outer tube ends can be mechanically deformed simultaneously to interlock with both end couplings, for easily, economically and reliably forming the finished HPLC column.

This invention offers several significant advantages over existing HPLC columns. For example, the inner tube can be economically fabricated in long lengths while yet having its bore machined and polished to the close finish and tolerance needed end to end. The outer tube can essentially be an off the shelf item, requiring no special machining. Both tubes can then be cut to the needed lengths to form a desired column, with only minor buffing of any raw edges. This construction procedure will be the same independently of the length of column needed.

Also, the maximum outer surface of the finished column will be substantially cylindrical end to end, even over the regions of the end couplings. This will greatly improve temperature control of the column along its length even when using conventional thermal heaters; and the column label, even for very short columns such as the 10 mm column, can be located over most if not all of the overall column length. Further, the deformed outer tube ends will lie hidden in the end coupling grooves, inwardly of the larger groove endward radial surface and its corner edge 62, to yield a high quality appearance, even with the disclosed rapid, efficient and effective securing structures and method.

This improved HPLC column design can be used to form different size columns, changing only the tube lengths and bore diameters, and absorbents, but still merely overlapping the inner and outer tubes and deforming the outer tube as noted. Further, the improved column will operate will conventional HPLC testing instruments, capillary lines and securing fittings.

While a single embodiment has been illustrated, minor changes could be made without departing from the inventive teaching. Accordingly, the invention is to limited only by the following claims.

What is claimed is:

1. A HPLC column ready to be connected and used in a liquid-tight serial flow circuit between capillary lines having externally threaded end fittings associated therewith, said column comprising an inner tube; absorbent filling the inner tube; a filter assembly across each inner tube end containing the absorbent; and end coupling members outwardly adjacent the filter assemblies;

a cylindrical outer tube overlying all of the inner tube and each filter assembly, and an inward portion of each coupling member, all arranged in an axially aligned association;

means cooperating between the outer tube and the underlying inward portion of each end coupling member for mechanically holding the outer tube and end coupling members together;

each end coupling having an internally threaded opening suited to cooperate with a respective threaded end fitting, each filter assembly having a sealing bore sized to cooperate in liquid-tight association with a respective capillary line, and the opening and bore being concentrically arranged suited for mechanically connecting the end fittings and capillary lines in said liquid-tight flow connection through the column via the inner tube, absorbent and filter assemblies; and the outer tube cylindrical outer surface defining the maximum outer radial dimension of the column.

2. A HPLC column according to claim 1, further wherein the inward portion of each end coupling member underlying the outer tube having an annular groove defined by axially separated generally radial surfaces and a generally axial bottom surface, the bottom groove surface being smaller in diameter than the inner face of the outer tube, and the outer tube proximate each end being configured conically to tightly fit in and terminate within the annular groove and providing the cooperating holding means between the outer tube and the each end coupling member for holding them together.

3. A HPLC column according to claim 2, further wherein said groove having a depth about equal to the wall thickness of the outer tube and having an axial width in excess of the wall thickness of the outer tube, whereby the outer tube end being at least partly hidden within the groove.

4. A HPLC column according to claim 3, further wherein the inward radial groove surface having an outer diameter less than the outer diameter of the outward radial groove surface and the outward radial groove surface having an outer diameter more than the inner diameter of the outer tube but less than the outer diameter of the outer tube.

* * * * *